United States Patent [19]

Glamkowski et al.

[11] 4,448,784
[45] May 15, 1984

[54] 1-(AMINOALKYLPHENYL AND AMINOALKYLBENZYL)-INDOLES AND INDOLINES AND ANALGESIC METHOD OF USE THEREOF

[75] Inventors: Edward J. Glamkowski, Warren, N.J.; James M. Fortunato, North Wales, Pa.

[73] Assignee: Hoechst-Roussel Pharmaceuticals, Inc., Somerville, N.J.

[21] Appl. No.: 367,707

[22] Filed: Apr. 12, 1982

[51] Int. Cl.³ ............... A61K 31/405; C07D 209/08
[52] U.S. Cl. ................................ 424/274; 548/491; 548/469
[58] Field of Search ............... 548/491, 469; 424/274

[56] References Cited

U.S. PATENT DOCUMENTS 4,186,199  1/1980  Glamkowski et al. ......... 424/274 X

OTHER PUBLICATIONS

Glamkowski et al., J. of Heterocyclic Chemistry, 16, pp. 865–869, (1979).

*Primary Examiner*—Paul M. Coughlan, Jr.
*Assistant Examiner*—David B. Springer
*Attorney, Agent, or Firm*—Jerome Rosenstock

[57] ABSTRACT

The invention relates to 1-(aminoalkylphenyl and aminoalkylbenzyl)indoles and indolines of the formula:

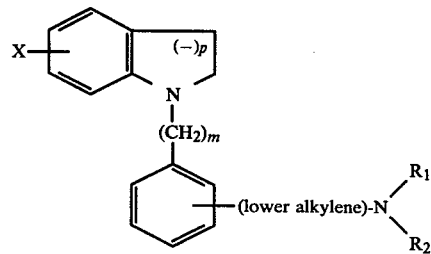

where $R_1$ and $R_2$ are the same or different and are hydrogen, lower alkyl, cycloalkyl and acyl of the formula

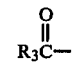

where $R_3$ is lower alkyl, lower alkoxy, cycloalkyl, phenyl of the formula

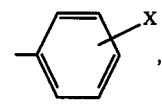

and Ar lower alkyl of the formula -lower alkylene

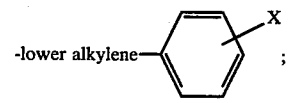

X is hydrogen, halogen, lower alkoxy, Ar lower alkoxy of the formula

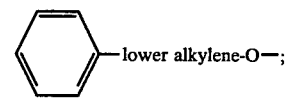

m and p are independently integers of 0 and 1 and the pharmaceutically acceptable acid addition salts thereof.

31 Claims, No Drawings

1-(AMINOALKYLPHENYL AND AMINOALKYLBENZYL)-INDOLES AND INDOLINES AND ANALGESIC METHOD OF USE THEREOF

To the best of our knowledge the compounds of the present invention have not heretofore been described or suggested.

The compounds of the present invention have the general formula

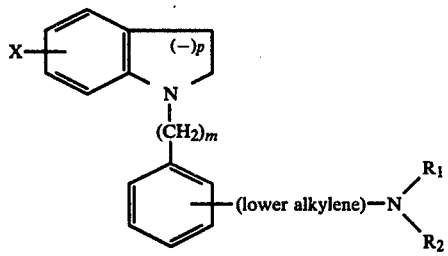

where $R_1$ and $R_2$ are the same or different and are hydrogen, lower alkyl, cycloalkyl and acyl of the formula

where $R_3$ is lower alkyl, lower alkoxy, cycloalkyl, phenyl of the formula

and Ar lower alkyl of the formula

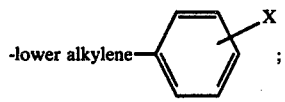

X is hydrogen, halogen, lower alkoxy, Ar lower alkoxy, of the formula

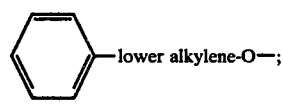

m and p are independently an integer of 0 or 1 and the pharmaceutically acceptable acid addition salts thereof.

In the above definitions the term "lower" means the group it is describing contains from 1 to 6 carbon atoms. The term "alkyl" refers to a straight or branched chain hydrocarbon containing no unsaturation, e.g. methyl, ethyl, isopropyl, 2-butyl, neopentyl, n-hexyl, etc.; the term "alkoxy" refers to a monovalent substituent which consists of an alkyl group linked through an ether oxygen having its free valence bond from the ether oxygen, e.g. methoxy, ethoxy, propoxy, butoxy, pentoxy, etc.; the term "cycloalkyl" refers to a monovalent substituent consisting of a saturated hydrocarbon group possessing at least one carbocyclic ring, of 3 to 7 carbon atoms, e.g. cyclopropyl, cyclobutyl, cyclopentyl, cyclohexyl, cycloheptyl, etc., having its free valence bond from a carbon of the carbocyclic ring; the term "Ar lower alkyl" refers to a monovalent substituent which consists of an aryl group, e.g., phenyl, p-nitrophenyl, o-tolyl, m-methoxy phenyl etc. linked through a lower alkylene group having its free valence bond from a carbon of the lower alkylene group, and having a formula of

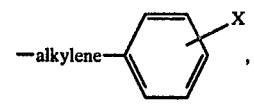

where X is as previously defined; the term "alkylene" refers to a bivalent radical of the lower branched or unbranched alkyl group it is derived from having valence bonds from two terminal carbons thereof, e.g. ethylene (—CH$_2$CH$_2$—), propylene (—CH$_2$CH$_2$CH$_2$—) isopropylene

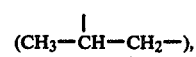

etc.; and the term "halogen" refers to a member of the family consisting of fluorine, chlorine, bromine and iodine.

The compounds of the present invention are prepared in the following manner. The substituents X, $R_1$, $R_2$ and $R_3$ and the integers m and p are as defined above unless indicated otherwise.

A. A substituted indoline or indole of the formula

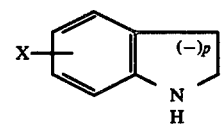

is selected. Compound (II) is reacted with a halobenzonitrile or a halo tolunitrile having the formula

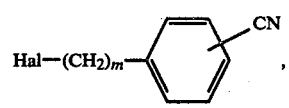

where Hal is a halogen selected from F, Cl, Br and I to form an intermediate of the invention.

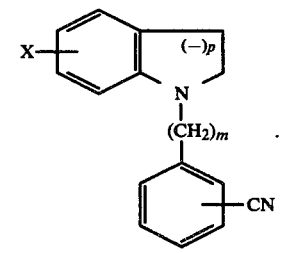

Compound IV is typically obtained by reacting compounds II and III under nucleophilic substitution reaction conditions. Typically, where p=1, compound II is reacted with compound III in the presence of a base, e.g. NaH, (CH₃)₃—C—OK, C₆H₅Li, and in a solvent, e.g., dimethylsulfoxide (DMSO), dimethylformamide (DMF), xylene, etc. at a temperature of 0° to 200° C. for 1 to 24 hours to form compound IV. Alternatively, where p=0, compound II is reacted with compound III in the presence of a base, e.g., K₂CO₃, NaHCO₃, or even an excess of the indoline II serving as base, etc, without or with an inert solvent, e.g., chloroform, methylene chloride, toluene etc. at a temperature of −10° to 100° C. for 1 to 24 hours to form compound IV.

Compound IV in turn is reduced by conventional means, e.g. with a metal hydride such as LiAlH₄, BH₃ etc. in an inert solvent such as tetrahydrofuran (THF), diethylether, dioxan, etc. at a temperature of −10° to 100° C. for 1 to 24 hours to reduce the cyano group to form a compound of the invention

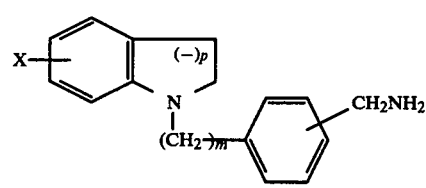
(V)

B. Compound IV is hydrolyzed in a conventional manner utilizing either an acidic or alkaline medium whereby the cyano group is hydrolyzed to a carboxyl group to give an intermediate of the invention having the formula

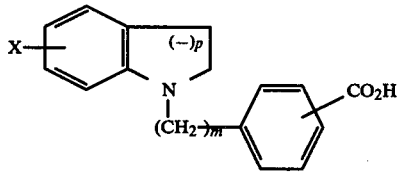
(VI)

Compound VI is reduced by reaction with a metal hydride, e.g. LiAlH₄, BH₃, AlH₃, etc., in an inert solvent, e.g. THF, ether, dioxan, etc, typically at a temperature of −10° to 100° C. for 1 to 24 hours to form an alcohol intermediate of the invention having the formula

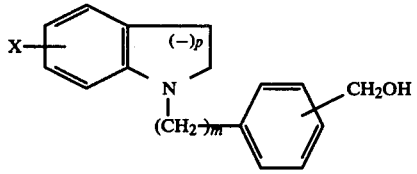
(VII)

Compound VII is, in turn, reacted with a sulfonyl halide of the formula R₄SO₂—Hal (VIII) where Hal is a halogen selected from F, Cl, Br and I, and R₄ is lower alkyl, e.g. methyl, or aryl such as phenyl or tolyl, to form a sulfonate intermediate of the invention having the formula

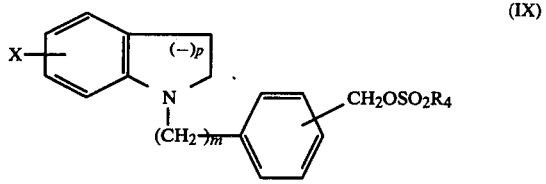
(IX)

where R₄ is lower alkyl, e.g. methyl, or phenyl. Typically compound VII is reacted with compound VIII in an inert solvent, e.g. dichloromethane, ether, etc. at a temperature of 0° to 100° C. for 1 to 24 hours to form compound IX. Compound IX is then reacted with an inorganic cyanide, e.g. NaCN, KCN, in a conventional manner in the presence of a solvent, typically an aprotic polar solvent such as methanol, ethanol, dimethyl formamide (DMF), N-methyl-2-pyrrolidone or dimethyl sulfoxide (DMSO), to form an intermediate of the invention having the formula

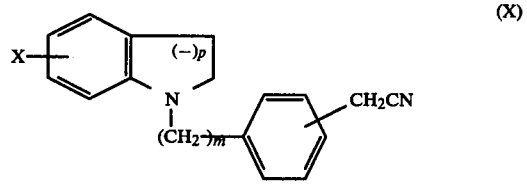
(X)

The cyano group of compound X is reduced in the manner previously described to form a compound of the invention having the formula

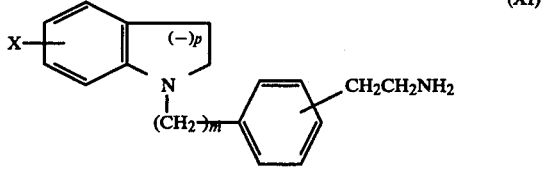
(XI)

C. Compound IV is reacted in a conventional manner with a Grignard reagent of the formula R₅ MgHal, (XII) where Hal is a halogen selected from Cl, Br and I and R₅ is an alkyl group of 1 to 5 carbon atoms, or phenyl to form an intermediate of the invention having the formula

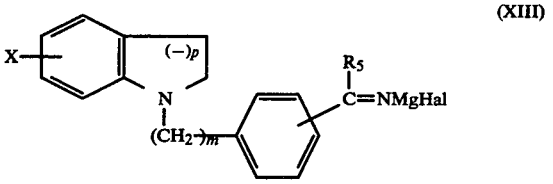
(XIII)

Typically, compound IV is reacted with the Grignard reagent (XII) in an inert solvent, e.g. tetrahydrofuran (THF), ether, dioxan etc., at a temperature of 0° to 100° C. for 1 to 24 hours to form compound XIII. Compound XIII is then reduced by reduction with metal halide, e.g. LiAlH₄, as previously described for the reduction of the cyano group, to form a compound of the invention having the formula

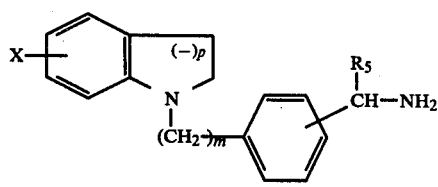

D. The N-alkyl or N-acyl derivatives of compounds V, XI and XIV are prepared in a conventional manner, as for example by reaction with a lower alkyl halide or a cycloalkyl halide or an acylhalide of the formula

where Hal is a halogen selected from F, Cl, Br and I and $R_3$ is as previously defined, whereby a mono- or bi-substituted compound of the invention, Compound I, is obtained where at least $R_1$ or $R_2$ is lower alkyl, cycloalkyl or acyl of the formula

Alternatively, compounds V, XI and XIV can be reacted in a conventional manner with an alkylchloroformate followed by reduction of the resultant compound, as with $LiAlH_4$, $NaBH_4$, to form compound I of the invention where at least $R_1$ or $R_2$ is methyl. In another alternative embodiment, compounds V, XI and XIV can be reacted in a conventional manner with an acid anhydride,

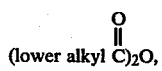

to form compound I of the invention where at least $R_1$ or $R_2$ is lower alkyl.

E. Where p is 1 in compound IV, it is typically reduced to compound IV where p is 0 by reaction with sodium cyanoborohydride. Typically this reaction is carried out in a solvent of THF, acetonitrile, or acetic acid at a temperature of 0° to 100° C. for 1 to 24 hours.

The compounds of the invention are useful as analgesic agents due to their ability to alleviate pain in mammals. The activity of the compound is demonstrated in the 2-phenyl-1,4-benzoquinone-induced writhing test in mice, a standard assay for analgesia [Proc. Soc. Exptl. Biol. Med., 95, 729 (1975)]. The analgesic activity of some of the compounds expressed in terms of percent inhibition of writhing is given in Table I.

TABLE I

| Compound | Dose (subcutaneous) mg/kg of body Weight | Inhibition Of writhing % |
|---|---|---|
| 3-(1-indolinyl)benzene-methanamine hydrochloride | 4.2 | 50 |
| 2-(1-indolinyl)benzene-methanamine hydrochloride | 14.1 | 50 |
| 4-(1-indolinyl)benzene-methanamine hydrochloride | 25.0 | 50 |
| 3-[5-chloro-1-indolinyl]benzene-methanamine hydrochloride | 4.7 | 50 |

TABLE I-continued

| Compound | Dose (subcutaneous) mg/kg of body Weight | Inhibition Of writhing % |
|---|---|---|
| 3-(1-indolyl)benzenemethanamine hydrochloride | 19.1 | 50 |
| 3-(5-chloro-1-indolinylmethyl)-benzenemethanamine fumarate | 20.2 | 50 |
| N—cyclopropylcarbonyl-3-(1-indolinyl)-benzenemethanamine | 10.0 | 59.0 |
| N—cyclopropylmethyl-3-(1-indolinyl)benzenemethanamine hydrochloride | 10.0 | 49.0 |
| N,N—dimethyl-3-(1-indolinyl)benzenemethanamine hydrochloride | 25.0 | 50.0 |
| 3-(1-indolinyl)-2-benzene ethanamine.½ fumarate | 10.0 | 57.0 |
| 3-(1-indolinyl)-α-methylbenzene-methanamine hydrochloride | 10.0 | 40.0 |
| propoxyphene | 3.9 | 50 |

The analgesic relief of pain is achieved when the compounds of the invention are administered to a subject requiring such treatment at an effective oral, parenteral or intravenous dose of from 1.0 to 25 mg/kg of body weight per day. A preferred effective dose within this range is from about 1 to 10 mg/kg of body weight per day. A particularly preferred effective amount is about 5 mg/kg of body weight per day. It is to be understood, however, that for any particular subject, specific dosage regimens should be adjusted according to the individual need. It is further to be understood that the dosages set forth herein are examples only and that they do not, to any extent, limit the scope of practice of the invention.

Effective amount of the compounds of the present invention may be administered to a subject by one of various methods, for example, orally as in capsules or tablets, parenterally in the form of sterile solutions or suspensions, and in some cases intravenously in the form of sterile solutions. The compounds of the invention, while effective themselves, may be formulated and administered in the form of their pharmaceutically acceptable acid addition salts for purposes of stability, convenience of crystallization, increased solubility and the like.

Preferred pharmaceutically acceptable acid addition salts include those derived from inorganic acids such as hydrochloric, hydrobromic, sulfuric, nitric, phosphoric, perchloric acids and the like as well as organic acids such as tartaric, citric, acetic, succinic, maleic, fumaric acids and the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the 1-(aminoalkylphenyl) or 1-(aminoalkyl benzyl)-indoles or indolines of the invention, the active ingredient, but may be varied depending upon the particular form and may conveniently be between 4% to about 70% of the weight of the unit. The amount of the compound present in such compositions is such that a suitable dosage will be obtained. Preferred compositions and preparations according to the present invention are prepared so that an oral dosage unit form contains between 5.0–300 milligrams of the 1-(aminoalkylphenyl and aminoalkylbenzyl)indoles and indolines of the invention.

The tablets, pills, capsules, troches and the like may also contain the following adjuvants: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of the 1-(aminoalkylphenyl and aminoalkylbenzyl) indoles and indolines of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the 1-(aminoalkylphenyl and aminoalkylbenzyl) indoles and indolines of the invention.

The solutions or suspensions may also include the following adjuvants: a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The following examples are for illustrative purposes and are not to be construed as limiting the invention disclosed herein. All temperatures are given in degrees centigrade.

EXAMPLE 1

2-(1-Indolinyl)benzonitrile

A stirred mixture of 61.63 g (0.509 mole) 2-fluorobenzonitrile and 125.6 ml (1.12 mole) indoline under nitrogen was heated at 170°–180° C. for 22.5 hours. The resulting suspension was transferred to a separatory funnel with the aid of 400 ml of $CH_2Cl_2$ and this solution was washed twice with water (400 ml), four times with 4 N HCl (450 ml), water (450 ml), brine (400 ml), dried ($Na_2SO_4$), and concentrated to give 78.6 g (71.5%) of a liquid. The crystals which formed on standing were filtered, washed with ether and dried at 42° C. under vacuum, thus affording 4.33 g (3.9% overall) of 2-(indolinyl)benzonitrile M.P. 94.0°–96.5° C.

ANALYSIS: Calculated for $C_{15}H_{12}N_2$: 81.79%C, 5.49%H, 12.72%N, Found: 81.60%C, 5.54%H, 12.65%N.

2-(1-Indolinyl) benzenemethanamine hydrochloride

A solution of 17.18 g (0.078 mole) of 2(1-indolinyl)-benzonitrile of Example 1a in 150 ml dry tetrahydrofuran (THF) was added dropwise to a rapidly stirred ice cold solution of $BH_3$ in THF (236 ml of 1 M solution; 0.236 mole) under nitrogen. At the end of the addition the resultant solution was permitted to warm to room temperature and stir for 3 hours and then heated at reflux for 50 minutes. The product was then cooled to 0° C., treated dropwise with 6 N HCl (100 ml), and permitted to stand overnight (about 16 hours) at room temperature. The reaction mixture was cooled to 0° C. and made basic using solid NaOH. The resulting aqueous layer was extracted with ether (200 ml) and the combined organic portions were washed twice with brine (200 ml portions), dried over $K_2CO_3$, and concentrated to afford 21.1 g of crude free base. The free amine was dissolved in dry ether (300 ml), cooled to 0° C., and treated with gaseous HCl. The resulting salt was filtered, washed with dry ether (300 ml), and dried under vacuum at 40° C. thus affording 19.25 g (94.4%) of crude salt, m.p. 226°–228° C. Recrystallization of 15.59 g of the crude salt from methanol-ether afforded 10.49 g (67.3% recovery) of 2-(1-indolinyl) benzenemethanamine hydrochloride, m.p. 231°–232° C.

ANALYSIS: Calculated for $C_{15}H_{16}N_2.HCl$: 69.09%C, 6.57%H, 10.74%N, Found: 68.85%C, 6.57%H, 10.64%N.

EXAMPLE 2

4-(1-Indolinyl)benzonitrile 4.94 g (0.206 mole) 99% NaH was added in one portion to a solution of 21.6 ml (0.188 mole) indoline in 85 ml sieve dried dimethylsulfoxide (DMSO) at room temperature. The resulting slurry was permitted to stir at room temperature for 2 hours and then cooled in an ice bath. A solution of 25 g (0.206 moles) 2-fluorobenzonitrile in 35 ml DMSO was added dropwise. At the end of the addition, the ice bath was removed and the mixture was permitted to stir at room temperature overnight (about 16 hours). The product was poured onto 300 ml of ice and extracted with $CHCl_3$ (300 ml). The organic phase was thrice washed with water (500 ml portions), brine (500 ml), dried ($Na_2SO_4$) and concentrated to give 39.9 g (96.4%) of crude material. Two recrystallizations from isopropyl ether afforded 4-(1-indolinyl)benzonitrile, m.p. 88.5°–89.5° C.

ANALYSIS: Calculated for $C_{15}H_{12}N_2$: 81.79%C, 5.49%H, 12.72%N, Found: 81.60%C, 5.52%H, 12.72%N.

b. 4-(1-Indolinyl)benzenemethanamine hydrochloride

A solution of 12.06 g (54.8 mmole) of 4-(1-indolinyl)-benzonitrile of Example 2a in 62 ml tetrahydrofuran (THF) was added dropwise to a rapidly stirred ice cold solution of $BH_3$ in THF (181 ml of 0.93 M solution, 3.07 equiv. 168.4 mmole) under nitrogen. After heating at reflux for 1.5 hours, the solution was permitted to cool to room temperature and stand overnight. The ice cold reaction mixture was then treated dropwise with 6 M aq. HCl (100 ml), heated at reflux for 40 minutes, cooled to 0° C., and made basic using solid NaOH. The resulting aqueous phase was extracted with ether and the combined organic portions (100 ml total) were washed with water (300 ml), twice with brine (300 ml portions) dried ($Na_2SO_4$) and concentrated to afford 13.2 g of crude free base. A solution of 7.5 g (33.4 mmole) of crude free base in 200 ml 1:1 ethanol-ether was treated with 50 ml of ethanolic HCl. 200 ml dry ether was added and the resulting solid was filtered, washed with dry ether, and dried thus giving 5.9 g (67.7%) of crude product. Recrystallization from hot ethanol-ether (charcoal) afforded 2.98 g of pure 4-(1-indolinyl)benzenemethanamine hydrochloride, m.p. 251.5°–252.5° C.

ANALYSIS: Calculated for $C_{15}H_{16}N_2.HCl$: 69.09%C, 6.57%H, 10.74%N, Found: 69.02%, 6.60%H, 10.66%N.

EXAMPLE 3

3-(1-Indolinyl)benzonitrile 4.63 g (0.0193 mole, 1.1 equiv.) 99% NaH was added in one portion to a stirred solution of 19.8 ml (0.175 mole) indoline in 90 ml sieve dried DMSO under nitrogen at room temperature. After 65 minutes, the mixture was cooled in an ice bath and treated dropwise with a solution of 23.43 g (0.193 mole, 1.1 equiv.) 3-fluorobenzonitrile in 34 ml dry DMSO. The product was permitted to stir overnight at room temperature, poured onto 300 ml ice and extracted with $CHCl_3$. The organic layer was washed five times with water (800 ml portions), dried over $MgSO_4$, and concentrated to give 42.75 1 g (38.6 g theory) of oil. 2.0 g of the crude product was chromatographed on silica gel (104 g) using ether-hexane thus affording a 0.99 g sample of an oil of pure 3-(1-indolinyl)benzonitrile.

ANALYSIS: Calculated for $C_{15}H_{12}N_2$: 81.79%C, 5.49%H, 12.72%N, Found: 81.76%C, 5.37%H, 12.59%N.

3-(1-Indolinyl)benzenemethanamine hydrochloride

A solution of 7.1 g (32.3 mmole) of 3-(1-indolinyl)benzonitrile of Example 3a in 44 ml THF was added dropwise over 30 minutes to an ice cold solution of 129 ml (129 mmole, 4 equivalents) of 1 M $BH_3.THF$ complex under nitrogen. After heating at reflux for 1 hour, the reaction mixture was cooled to 0°–5° C. and treated dropwise with 50 ml concentrated HCl. The resulting suspension was heated at reflux for 1 hour, permitted to stand at room temperature overnight (about 16 hours) and then made basic using 50% NaOH (60 ml). The reaction mixture was partitioned between water—$CH_2Cl_2$ (300 ml each) and the organic phase was washed with brine (300 ml), dried over $MgSO_4$ and concentrated to give 8.9 g of crude free base. Conversion as in Example 1 to the HCl salt (ethanol/ethereal HCl) and recrystallization from hot acetonitrile-methanol afforded 2.86 g (34% overall) of 3-(1-indolinyl)benzenemethanamine hydrochloride, m.p. 170.5°–173.5° C.

ANALYSIS: Calculated for $C_{15}H_{16}N_2.HCl$: 69.09%C, 6.57%H, 10.74%N, Found: 69.13%C, 6.64%H, 10.78%N.

EXAMPLE 4

3-(5-Chloro-1-indolinyl)benzonitrile

A slurry of 2.64 g (0.11 mole, 1.1 equivalents) sodium hydride in 15.36 g (0.1 mole) 5-chloroindoline and 50 ml sieve dried DMSO was permitted to stir at room temperature under nitrogen for 2 hours. While cooling in an ice bath, a solution of 12.11 g (0.1 mole) 3-fluorobenzonitrile in 15 ml sieve dried DMSO was then added dropwise over 15 minutes. At the end of the addition, the ice bath was removed and the reaction mixture was permitted to warm to room temperature and stir overnight (20 hours). The product was poured onto ice and then extracted twice with $CHCl_3$. The combined organic portions (400 ml) were washed four times with water (400 ml portions), 4 N HCl (three 300 ml portions) brine (300 ml), dried over $Na_2SO_4$, and concentrated to give 28.03 g (25.47 g theory) of a solid. Recrystallization from hot absolute ethanol containing 5–10% $CHCl_3$ afforded 11.12 g (43.66% overall) of 3-(5-chloro-1-indolinyl)benzonitrile, m.p. 120°–121° C.

ANALYSIS: Calculated for $C_{15}H_{11}ClN_2$: 70.73%C, 4.35%H, 13.92%Cl, 11.00%N, Found: 70.46%C, 4.40%H, 14.07%Cl, 10.82%N.

b. 3-(5-Chloro-1-indolinyl)benzenemethanamine hydrochloride

A solution of 10.66 g (41.85 mmole) of 3-(5-chloro-1-indolinyl)benzonitrile of Example 4a in 100 ml dry THF was added dropwise to an ice cold rapidly stirred slurry of 6.35 g (167.4 mmole, 4 equiv.) $LiAlH_4$ in 100 ml dry THF under nitrogen. After heating at reflux for 2 hours, the reaction mixture was cooled in an ice bath and treated dropwise with 6 ml $H_2O$, 6 ml 10% NaOH and 18 ml $H_2O$. The resulting salts were filtered and washed with hot $CHCl_3$. The filtrate was concentrated and the residue was dissolved in $CHCl_3$ (200 ml), washed with brine (400 ml), dried over $Na_2SO_4$, and concentrated to give 10.22 g (94.4%) of free base. The resultant base was converted to the HCl salt (isopropanol-ethereal HCl) as in Example 1, and recrystallized from hot isopropanol-methanol to give 9.09 g (73.6% overall) of 3-(5-chloro-1-indolinyl)benzenemethanamine hydrochloride, m.p. 220°–222° C.

ANALYSIS: Calculated for $C_{15}H_{15}ClN_2.HCl$: 61.03%, 5.46%H, 9.49%N, Found: 61.26%C, 5.50%H, 9.57%N.

EXAMPLE 5 a. α-(1-Indolinyl)-m-tolunitrile

An ice cold slurry of 10.6 g (76.9 mmole) $K_2CO_3$ in 8.6 ml (76.9 mmole) indoline and 50 ml sieve dried dimethylformamide (DMF) was treated dropwise with a solution of 15 g (76.9 mmole) α-bromo-m-tolunitrile in 75 ml sieve dried DMF. After stirring for 2 hours at room temperature, the reaction mixture was filtered and concentrated under high vacuum (55° C.). The residue was dissolved in $CHCl_3$ (150 ml) and washed twice with water (250 ml portions), brine (250 ml), dried over $Na_2SO_4$, and concentrated to give 15.28 g (84.8%) of crude nitrile. Recrystallization from hot ethanol gave 10.70 g (59.4% overall) of product, m.p. 54°–56° C. A second recrystallization of a 5.0 g sample afforded 2.74 g of α-(1-indolinyl)-m-tolunitrile, m.p. 54.5°–56.0° C.

ANALYSIS: Calculated for $C_{16}H_{14}N_2$: 82.02%C, 6.02%H, 11.96%N, Found: 82.07%C, 5.96%H, 11.94%N.

b. 3-(1-Indolinylmethyl)benzenemethanamine dihydrochloride

A solution of 13.09 g (55.87 mmole) of α-(1-indolinyl)-m-tolunitrile of Example 5a in 120 ml distilled THF was added dropwise to a rapidly stirred ice cold slurry of 8.48 g (223.5 mmole, 4 equivalents) of LiAlH$_4$ in 110 ml distilled THF. After heating at reflux for 18 hours, the reaction mixture was cooled to 0.5° C. and treated dropwise with 8.5 ml water, 8.5 ml 10% NaOH, and 25.5 ml H$_2$O. The salts were filtered, washed thrice with 100 ml hot CH$_2$Cl$_2$, and the filtrate was concentrated. The residue was dissolved in CHCl$_3$ and washed with dilute aqueous NaOH, with brine, dried (Na$_2$SO$_4$), and concentrated to give 12.71 g (95.4%) of free base. A 4.85 g portion of the free base was converted to the hydrochloride salt as in Example 1 (ethanol-ether/ethereal HCl) thus giving 5.75 g of 3-(1-indolinylmethyl)benzenemethanamine dihydrochloride, m.p. 160° C. dec.

ANALYSIS: Calculated for C$_{16}$H$_{18}$N$_2$.2HCl: 61.74%C, 6.48%H, 9.00%N, Found: 61.54%C, 6.38%H, 8.70%N.

EXAMPLE 6 a. 3-(5-Chloro-1-indolyl)benzonitrile

To a stirred solution under nitrogen of 7.58 g (0.050 mole) of 5-chloroindole in 50 ml of dimethylsulfoxide (DMSO) was added 1.51 g (0.063 mole) of sodium hydride in portions over a 0.5 hour period. When no more bubbles of hydrogen were visible (after 5 hours) a solution of 7.63 g (0.063 mole) of 3-fluorobenzonitrile in 10 ml DMSO was added dropwise over 1 hour. The solution was stirred overnight, and then heated at 100° C. for 3 hours to complete the reaction. After cooling, the reaction fluids were slowly decanted into 1 liter of ice/water, with good stirring. This caused the product to separate as chunks of a semi-solid. After 2 hours, the mixture was filtered and the cake washed repeatedly with water. This material was dissolved in 130 ml of boiling ethanol, charcoaled, filtered and allowed to stand overnight (about 16 hours). The crystals were collected, washed with ethanol, dried to afford 6.60 g of product (52.4%), having m.p. 116°–120° C. Recrystallization from ethanol gave 3-(5-chloro-1-indolyl)benzonitrile in an overall yield of 42%, m.p. 120°–122° C.

ANALYSIS: Calculated for C$_{15}$H$_9$ClN$_2$: 71.30%C, 3.59%H, 11.09%N, Found: 71.29%C, 3.50%H, 11.17%N.

b. 3-(5-Chloro-1-indolyl)benzenemethanamine hydrochloride

To a stirred mixture of 1.67 g of lithium aluminum hydride in 100 ml of dry tetrahydrofuran (THF), kept at 0°–5° C. under nitrogen, was added dropwise a solution of 5.60 g (0.022 mole) of 3-(5-chloro-1-indolyl)benzonitrile of Example 6a in 150 ml of THF. The mixture was stirred 1 hour more at 0° C., 1 hour at room temperature, and then refluxed for 5 hours. After cooling to 0° C., the reaction was quenched by slow and cautious addition of a solution of 25 ml of water in 25 ml of THF. The resulting mixture was stirred 1 hour at room temperature before filtering to remove the inorganic salts. The filtrate was concentrated to an oily residue which was partitioned between 250 ml of dichloromethane and 250 ml of water. The organic phase was separated and extracted twice more with water before drying over Na$_2$SO$_4$ and concentrating to an oil (5.8 g). This was dissolved in 20 ml of absolute ethanol and the stirred solution treated with 100 ml of ethereal hydrogen chloride. The salt was collected and found to weigh 5.2 g (81% overall yield) m.p. 195° C.-sinter, 220°–228° C. melting. Recrystallization from boiling ethanol (charcoal) furnished 2.4 g (37% yield) of 3-(5-chloro-1-indolyl)benzenemethanamine hydrochloride, m.p. 230°–233° C.

ANALYSIS: Calculated for C$_{15}$H$_{13}$ClN$_2$.HCl: 61.45%C, 4.81%H, 9.55%N, Found: 61.33%C, 4.90%H, 9.66%N.

EXAMPLE 7 a. 3-(1-Indolyl)benzonitrile

To a stirred solution, under nitrogen, of 17.6 g (0.150 mole) of indole in 100 ml of dry dimethylsulfoxide (DMSO) was added 4.5 g (0.188 mole) of sodium hydride in portions over a 1.5 hour period. When no more bubbles of hydrogen were visible (4–5 hours), there was added dropwise a solution of 22.8 g (0.188 mole) of 3-fluorobenzonitrile in 25 ml of dry DMSO. When the addition was complete (1 hour) the mixture was stirred overnight (about 16 hours) and then 3 hours at 100° C. The cooled mixture was poured into 1.5 liters of stirred water-ice mixture to precipitate a semi-solid. The supernatent was poured off and the coagulated material was washed several times more with water. It was then dissolved in 500 ml of dichloromethane, washed twice with dilute brine, dried over Na$_2$SO$_4$, and concentrated in vacuo to an oil. This material weighed 32 g (100% yield). A portion was distilled yielding 3-(1-indolyl)benzonitrile (160°/0.1 mm) in 75% overall yield. The product was a soft, crystalline material at room temperature, m.p. 33°–36° C.

ANALYSIS: Calculated for C$_{15}$H$_{10}$N$_2$: 82.55%C, 4.62%H, Found: 82.29%C, 4.56%H.

b. 3-(1-Indolyl)benzenemethanamine hydrochloride

To a stirred mixture, kept at 0°–5° C. under nitrogen, of 3.8 g of lithium aluminum hydride in 150 ml of dry tetrahydrofuran was added dropwise a solution of 10.9 g (0.050 mole) of 3-(1-indolyl)benzonitrile of Example 7a in 50 ml of THF. When the addition was complete (1 hour), the mixture was stirred 1 hour at 0° C., 1 hour at room temperature and finally refluxed overnight. The mixture was then kept below 5° C. during cautious addition of a solution of 25 ml H$_2$O and 25 ml THF. After the addition, the mixture was stirred at room temperature for 2 hours, filtered, the cake washed twice with THF, and the combined filtrates concentrated. The residue was dissolved in 250 ml of dichloromethane and this solution was washed twice with dilute brine, dried over Na$_2$SO$_4$ and concentrated to an oil weighing 11.0 g (100%). The oil was dissolved in 25 ml of absolute methanol, and then treated in one portion with 50 ml of ether saturated with HCl gas. To the initial solution was added another 50 ml of ether. The salt crystallized rapidly and was immediately filtered, washed well with ether, and dried to yield 11.6 g (90%) of product, m.p. 189°–191° C. Recrystallization from isopropanol gave 10.0 g (78% overall yield) of pure 3-(1-indolyl)benzenemethanamine hydrochloride, m.p. 190°–192° C.

ANALYSIS: Calculated for C$_{15}$H$_{14}$N$_2$.HCl: 69.64%C, 5.84%H, 10.83%N, Found: 69.87%C, 5.71%H, 10.99%N.

EXAMPLE 8 a. N-Ethoxycarbonyl-3-(1-indolinyl)benzenemethanamine

A slurry of 10.0 g (39.3 mmole of 3-(1-indolinyl)benzenemethanamine hydrochloride of Example 3b in 120 ml CH$_2$Cl$_2$ was cooled in an ice bath and treated dropwise with a solution of 13.5 ml (95.8 mmole, 2.5 equivalents) of triethylamine in 40 ml CH$_2$Cl$_2$. After stirring for ten minutes, the resulting mixture was treated dropwise with a solution of 5.5 ml (57.5 mmole, 1.5 equivalents) ethylchloroformate in 40 ml CH$_2$Cl$_2$, permitted to warm to room temperature and stir overnight. 100 ml water were added and, after stirring for 45 minutes, the organic phase was separated, washed twice with 300 ml 2 N HCl, 300 ml H$_2$O, 300 ml brine, dried (Na$_2$SO$_4$), and concentrated to give 10.67 g (93.9%) of an oil. Kugelrohr distillation of a 4.35 g portion afforded 3.45 g of N-ethoxycarbonyl-3-(1-indolinyl)benzenemethanamine, bp 200°–208° C./0.1 mm.

ANALYSIS: Calculated for C$_{18}$H$_{20}$N$_2$O$_2$: 72.95%C, 6.80%H, 9.45%N, Found: 72.70%C, 6.75%H, 9.36%N.

b. 3-(1-Indolinyl)-N-methyl benzenemethanamine hydrochloride

A solution of 6.8 g (22.9 mmole) of N-ethoxycarbonyl-3-(1-indolinyl)benzenemethanamine of Example 8a in 45 ml distilled THF was added dropwise over 0.5 hours to a rapidly stirred, salt-ice cooled slurry of 3.5 g (91.8 mmole, 4.0 equivalents) LiAlH$_4$ in 100 ml THF. After warming to room temperature, the mixture was heated under reflux for 2.25 hours. The ice cold product was treated dropwise with 3.5 ml water, 7.0 ml 10% NaOH, and 7.0 ml water. The salts were filtered and washed with 125 ml boiling chloroform. The filtrate was concentrated and the residue was dissolved in 100 ml chloroform, washed with brine (300 ml), dried over Na$_2$SO$_4$, and concentrated to give 5.27 g (96.6%) of free base. The hydrochloride salt was formed in the same manner as in Example 1 (ether-methylene chloride/ethereal HCl) and recrystallized from hot isopropanol-ether to afford 3.79 g (60.3% overall) of 3-(1-indolinyl)-N-methyl benzenemethanamine hydrochloride, m.p. 149.0°–150.5° C.

ANALYSIS: Calculated for C$_{16}$H$_{18}$N$_2$.HCl: 69.94%C, 6.97%H, 10.19%N, Found: 69.89%C, 6.99%H, 10.02%N.

EXAMPLE 9 a. 3-(5-Methoxy-1-indolyl)benzonitrile

To a stirred solution, under nitrogen of 14.7 g (0.100 mole) of 5-methoxyindole in 100 ml of dry dimethylsulfoxide (DMSO) was added 3.0 g (0.125 mole) of sodium hydride in portions over a 0.5 hour period. When no more bubbles due to liberation of hydrogen gas were observed (after 5 hours), a solution of 15.1 g (0.125 mole) of 3-fluorobenzonitrile in 15 ml of DMSO was added dropwise over 0.5 hours. After stirring at room temperature overnight, the reaction was completed by heating at 100° C. for 2 hours. The mixture was cooled and added slowly to 2 liters of ice-water, with good stirring. This caused the product to separate as finely divided particles. These were filtered and the cake dissolved in 250 ml of dichloromethane. This solution was extracted twice with brine, dried over Na$_2$SO$_4$, and concentrated in vacuo to an oil (22.5 g) which began to crystallize. This was boiled and triturated with 25 ml ethanol to provide 18.3 g (74%) of a solid, m.p. 106°–112° C. Recrystallization from ethanol furnished 14.7 g (59% overall yield) of product, m.p. 110°–113° C. A sample was recrystallized again from ethanol to yield 3-(5-methoxy-1-indolyl)benzonitrile, m.p. 113°–115° C.

ANALYSIS: Calculated for C$_{16}$H$_{12}$N$_2$O: 77.40%C, 4.87%H, 11.28%N, Found: 77.40%C, 5.01%H, 11.40%N.

b. 3-(5-Methoxy-1-indolyl)benzenemethanamine hydrochloride

To a stirred mixture of 2.28 g of lithium aluminum hydride in 100 ml of dry tetrahydrofuran (THF), kept at 0° under nitrogen, was added dropwise a solution of 7.45 g (0.030 mole) of 3-(5-methoxy-1-indolyl)benzonitrile of Example 9a in 40 ml of THF. When the addition was complete (1 hour) the mixture was stirred 1 hour longer at 0° C., 1 hour at room temperature and then refluxed for 5 hours. After cooling back down to 0° C., the reaction was quenched by slow and cautious addition of a solution of 20 ml of water in 20 ml of THF. The resulting mixture was stirred 1 hour at room temperature before filtering to remove salts. The filtrate was concentrated to a residue which was partitioned between 200 ml of dichloromethane and 200 ml of water. The organic phase was separated and extracted twice with dilute brine before drying over Na$_2$SO$_4$. After concentration of the organic phase in vacuo there was obtained 7.2 g (95%) of oil. The hydrochloride salt of this material was prepared in the following manner. The oil was dissolved in 25 ml of methanol, and with good stirring, 100 ml of ethereal hydrogen chloride was added. The salt crystallized and was collected, washed well with ether and dried to yield 5.5 g (63%), m.p. 205°–209° C. This was recrystallized from 55 ml of hot ethanol (charcoal) to afford 2.3 g (27% overall yield) of 3-(5-methoxy-1-indolyl)benzenemethanamine hydrochloride, m.p. 209°–212° C.

ANALYSIS: Calculated for C$_{16}$H$_{16}$N$_2$O.HCl: 66.55%C, 5.93%H, 9.70%N. Found: 66.43%C, 5.76%H, 9.71%N.

EXAMPLE 10 a. 3-(5-Methoxy-1-indolinyl)benzonitrile

A solution of 4.0 g (16.1 mmole) of 3-(5-methoxy-1-indolyl)benzonitrile of Example 9a in 160 ml glacial acetic acid under nitrogen at 15°–20° C. was treated with 3.14 g (49.9 mmole, 3.1 equivalents) sodium cyanoborohydride. The reaction mixture was permitted to warm to room temperature and stir overnight (about 16 hours). The resulting solution was poured over ice (200 ml), made basic using 50% NaOH (165 ml) and extracted with chloroform (350 ml total). The combined organic extracts were washed with water (400 ml), brine (400 ml), dried over Na$_2$SO$_4$, and concentrated to give 3.90 g (96.8%) of the crude indoline as an oil. Crystallization from hot ethyl acetate-hexane afforded 1.87 g (46.4% overall) of 3-(5-methoxy-1-indolinyl)benzonitrile, m.p. 92.5°–93.5° C.

ANALYSIS: Calculated for C$_{16}$H$_{14}$N$_2$O: 76.78%C, 5.64%H, 11.19%N, Found: 76.62%C, 5.80%H, 11.24%N.

b. 3-(5-Methoxy-1-indolinyl)benzenemethanamine hydrochloride

A solution of 2.84 g (11.3 mmole) of 3-(5-methoxy-1-indolinyl)benzonitrile of Example 10a in 35 ml distilled THF was added dropwise over 1.25 hours to a rapidly stirred ice cold slurry of 1.72 g (45.4 mmole, 4.0 equivalents) LiAlH$_4$ in 50 ml distilled THF under nitrogen. After warming to room temperature, the mixture was heated under reflux for 2.25 hours, cooled in an ice bath, and quenched by dropwise addition of 2 ml water, 3 ml 10% NaOH, and 5 ml water. The salts were filtered and washed with boiling methylene chloride (200–259 ml). The filtrate was concentrated and the residue was dissolved in methylene chloride (150 ml) and washed with brine (250 ml), dried over $Na_2SO_4$, and concentrated to give 2.71 g (94.3%) of crude free base. Conversion to the hydrochloride salt (ether/ethereal HCl) as in Example 1, and recrystallization from isopropanol-ether afforded 2.10 g (63.9%) of 3-(5-methoxy-1-indolinyl)benzenemethanamine hydrochloride, m.p. 195.5° C. dec.

ANALYSIS: Calculated for $C_{16}H_{18}N_2O\cdot HCl$: 66.09%C, 6.59%H, 9.63%N, Found: 66.20%C, 6.61%H, 9.56%N.

EXAMPLE 11

N-Cyclopropylcarbonyl-3-(1-indolinyl)benzenemethanamine

A rapidly stirred ice cold slurry of 16.59 g (63.62 mmole) of 3-(1-indolinyl)benzenemethanamine hydrochloride of Example 3b in 300 ml $CH_2Cl_2$ was treated dropwise over 15 minutes with a solution of 20.6 ml (146.33 mmole, 2.3 equivalents) triethylamine in 25 ml $CH_2Cl_2$. After stirring for 10 minutes, a solution of 6.9 ml (76,34 mmole, 1.2 equivalents) cyclopropanecarboxylic acid chloride in 20 ml $CH_2Cl_2$ was added dropwise over 27 minutes. After stirring for 2 hours at room temperature, 75 ml water was added and the organic phase was separated and washed twice with 2 N HCl (300 ml), once with 5% NaOH (400 ml), once with brine (400 ml), dried over $Na_2SO_4$, and concentrated to give 18.8 g of crude amide. Column chromatography of a 4.93 g portion on silica gel using ether-hexane afforded 4.03 g (81.7%) of N-cyclopropylcarbonyl-3-(1-indolinyl)benzenemethanamine oil.

ANALYSIS: Calculated for $C_{19}H_{20}N_2O$: 78.05%C, 6.90%H, 9.58%N, Found: 78.00%C, 6.67%H, 9.69%N.

EXAMPLE 12

3-(1-Indolinyl)-N-phenylacetyl benzenemethanamine

A rapidly stirred ice cold slurry of 16.41 g (62.93 mmole) 3-(1-indolinyl)benzenemethanamine hydrochloride of Example 3b in 300 ml $CH_2Cl_2$ was treated dropwise over 16 minutes with a solution of 20.4 ml (144.74 mmole, 2.3 equivalents) triethylamine in 25 ml $CH_2Cl_2$. A solution of 10.0 ml (75.5 mmole, 1.2 equivalents) phenylacetyl chloride in 20 ml $CH_2Cl_2$ was then added dropwise over 17 minutes. After stirring for 2 hours at room temperature, 75 ml water was added and the organic phase was separated and washed twice with 2 N HCl, once with 5% NaOH, twice with brine, dried over $Na_2SO_4$, and concentrated to give 23.98 g of crude amide (bp>250° C./0.1 mm.). A 5.61 g portion was chromatographed on 90 g of silica gel using hexane-methylene chloride to give 2.89 g (51.5%) of 3-(1-indolinyl)-N-phenylacetyl benzenemethanamine.

ANALYSIS: Calculated for $C_{23}H_{22}N_2O$: 80.67%C, 6.48%H, 8.18%N, Found: 80.46%C, 6.45%H, 8.00%N.

EXAMPLE 13

N-Cyclopropylmethyl-3-(1-indolinyl)benzenemethanamine hydrochloride

A solution of 10.29 g (36.19 mmole) of N-cyclopropylcarbonyl-3-(1-indolinyl)benzenemethanamine of Example 11 in 50 ml THF was added dropwise over 50 minutes to an ice cold rapidly stirred slurry of 1.00 g (26.4 mmole, 0.75 equiv.) $LiAlH_4$ in 50 ml THF under nitrogen. After heating under reflux for 23 hours, considerable starting material was evident by thin layer chromatography (TLC) (silica gel 5% methanol in ether). The reaction mixture was cooled in an ice bath and treated with an ice cold slurry of 1.0 g (0.75 equivalents) $LiAlH_4$ in 40 ml THF. After heating under reflux for five hours an additional 2.0 g (1.5 equivalents) $LiAlH_4$ was added as a cold slurry in THF. Total $LiAlH_4$ charge was 4.0 g (105.4 mmole, 3.0 equivalents); total reflux time was 30 hours. Finally, the ice cold reaction mixture was treated dropwise with 4 ml water, 8 ml 10% NaOH, and 8 ml $H_2O$. The salts were filtered, washed with boiling methylene chloride (400 ml), and the filtrate was concentrated. The residue was dissolved in methylene chloride (100 ml), washed with brine (250 ml), dried over $Na_2SO_4$ and concentrated to give 8.44 g (86.2%) of crude free base. Conversion to the hydrochloride salt (ether/ethereal HCl), utilizing the procedure as in Example 1 and recrystallization from hot isopropanol yielded 4.00 g (36.1% overall) of N-cyclopropylmethyl-3-(1-indolinyl)benzenemethanamine hydrochloride, m.p. 156.5°–158.0° C.

ANALYSIS: Calculated for $C_{19}H_{22}N_2\cdot HCl$: 72.48%C, 7.36%H, 8.90%N, Found: 72.34%C, 7.25%H, 8.72%N.

EXAMPLE 14

3-(1-Indolinyl)-N-(2-phenylethyl)benzenemethanamine hydrochloride

A solution of 15.53 g (45.35 mmole) of 3-(1-indolinyl)-N-phenylacetylbenzenemethanamine of Example 12 in 65 ml distilled THF was added dropwise over 30 minutes to an ice-salt cooled, rapidly stirred slurry of 10.44 g (275.1 mmole, 6.07 equivalents) $LiAlH_4$ in 275 ml distilled THF under nitrogen. After warming to room temperature and stirring for 2 hours, the reaction mixture was heated under reflux for 19 hours and then quenched at 0° C. with 20 ml ice water-THF (1:1), 10 ml 10% NaOH, and 30 ml water. The salts were filtered, washed with $CHCl_3$ and the filtrate was concentrated. The residue was dissolved in $CHCl_3$, washed with brine, dried over $Na_2SO_4$, and concentrated to give 11.70 g (78.6%) of crude free base. Conversion to the HCl salt (ether/ethereal HCl) using the procedure of Example 1 gave 11.43 g (69.1%). Recrystallization from hot absolute ethanol gave 2.88 g (17.4% overall) of 3-(1-indolinyl)-N-(2-phenylethyl)benzenemethanamine hydrochloride, m.p. 188°–190° C.

ANALYSIS: Calculated for $C_{23}H_{21}N_2\cdot HCl$: 75.70%C, 6.90%H, 7.86%N, Found: 75.86%C, 6.60%H, 7.61%N.

EXAMPLE 15

N-Ethoxycarbonyl-3-(1-indolinyl)-N-methylbenzenemethanamine

An ice cold rapidly stirred solution of 7.73 g (28.18 mmole) of 3-(1-indolinyl)-N-methyl benzenemethanamine hydrochloride of Example 8b in 150 ml $CH_2Cl_2$ was treated dropwise with a solution of 9.9 ml (70.45 mmole, 2.5 equivalents) of triethylamine in 10 ml $CH_2Cl_2$. After stirring for three minutes, a solution of 4.0 ml (42.27 mmole, 1.5 equivalents) ethyl chloroformate in 10 ml $CH_2Cl_2$ was added dropwise. At the end of the addition the reaction mixture was permitted to warm to room temperature, stirred for 1 hour and stand about 64 hours. Water (200 ml) was added and the organic layer was separated and washed with 2 N HCl (200 ml), water (300 ml), brine (300 ml), dried (Na$_2$SO$_4$), and concentrated to give 7.64 g (87.3%) of crude product. Chromatography on silica gel (85 g) using ether-methylene chloride afforded 6.73 g (76.9% overall) of an oil of N-ethoxycarbonyl-3-(1-indolinyl)-N-methylbenzenemethanamine, bp>240° C./0.1 mm.

ANALYSIS: Calculated for C$_{19}$H$_{22}$N$_2$O$_2$: 73.52%C, 7.14%H, 9.02%N, Found: 73.52%C, 7.05%H, 8.74%N.

EXAMPLE 16

N,N-Dimethyl-3-(1-indolinyl)benzenemethanamine hydrochloride

A solution of 4.17 g (13.4 mmole) of N-ethoxycarbonyl-3-(1-indolinyl)-N-methylbenzenemethanamine of Example 15 in 20 ml distilled THF was added dropwise over 30 minutes to an ice cold rapidly stirred slurry of 2.04 g (53.7 mmole, 4.0 equivalents) of LiAlH$_4$ in 55 ml distilled THF under nitrogen. After heating under reflux for 2 hours, the reaction mixture was cooled in an ice bath and carefully treated dropwise with 2 ml water, 2 ml 10% NaOH, and 6 ml water. The salts were filtered, washed with hot methylene chloride (300 ml) and the filtrate was concentrated. The residue was dissolved in CHCl$_3$ (75 ml), washed with brine, dried over Na$_2$SO$_4$ and concentrated to give 3.26 g (96.4%) of the crude free base as an oil. Conversion to the hydrochloride salt (ether/ethereal HCl), utilizing the procedure of Example 1, and recrystallization from hot methanol-isopropanol afforded 2.82 g (72.9% overall) of N,N-dimethyl-3-(1-indolinyl)benzenemethanamine hydrochloride, m.p. 203°–204° C.

ANALYSIS: Calculated for C$_{17}$H$_{20}$N$_2$.HCl: 70.70%C, 7.33%H, 9.70%N, Found: 70.42%C, 7.53%H, 9.45%N.

EXAMPLE 17 a. α-(5-Chloro-1-indolinyl)-m-tolunitrile

A solution of 5.17 g (26.5 mmole) α-bromo-m-tolunitrile in 45 ml sieve dried dimethylformamide (DMF) was added dropwise over 20 minutes to an ice cold, rapidly stirred slurry of 4.07 g (26.5 mmole) 5-chloroindoline and 3.66 g (26.5 mmole) potassium carbonate in 25 ml sieve dried DMF under nitrogen. After warming to room temperature and stirring for 5 hours, the solvent was removed under high vacuum (50°–60° C.). The residue was partitioned between chloroform and water and the organic phase was separated, washed with water, brine, dried over Na$_2$SO$_4$, and concentrated to give 6.95 g (97.6%) of product. Recrystallization from hot absolute ethanol afforded 5.10 g (71.6% overall) of α-(5-chloro-1-indolinyl)-m-tolunitrile, m.p. 73.5°–75.5° C.

ANALYSIS: Calculated for C$_{16}$H$_{13}$ClN$_2$: 71.51%C, 4.88%H, 13.19%Cl, 10.42%N, Found: 71.45%C, 4.91%H, 13.00%Cl, 10.49%N.

b. 3-(5-Chloro-1-indolinylmethyl)benzenemethanamine fumarate

A solution of 4.41 g (16.4 g mmole) of α-(5-chloro-1-indolinyl)-m-tolunitrile of Example 17a in 30 ml distilled THF was added dropwise over 30 minutes to a rapidly stirred ice cold slurry of 2.49 g (65.6 mmole, 4.0 equivalents) LiAlH$_4$ in 65 ml distilled THF under nitrogen. After warming to room temperature, the mixture was heated under reflux for 2.75 hours, cooled in an ice bath, and quenched by dropwise addition of 2.5 ml water, 2.5 ml 10% NaOH, and 7.5 ml water. The salts were filtered and washed with 250 ml boiling methylene chloride. The filtrate was concentrated and the residue was dissolved in methylene chloride (100 ml), washed with brine (250 ml), dried over K$_2$CO$_3$, and concentrated to give 4.29 g (95.9%) of crude free base. The free base (4.23 g, 15.5 mmole) was dissolved in 30 ml absolute ethanol and added to a warm solution of 1.80 g (15.5 mmole) fumaric acid in 80 ml absolute ethanol. The fumarate salt slowly crystallized upon cooling to room temperature, thus affording 5.12 g (84.9%) of 3-(5-chloro-1-indolinylmethyl)benzenemethanamine fumarate, m.p. 178° C., dec.

ANALYSIS: Calculated for C$_{16}$H$_{17}$N$_2$Cl.C$_4$H$_4$O$_4$: 61.78%C, 5.44%H, 9.12%Cl, 7.20%N, Found: 61.82%C, 5.45%H, 9.10%Cl, 7.23%N.

EXAMPLE 18 a. 3-(5-Benzyloxy-1-indolyl)benzonitrile

To a rapidly stirred solution of 15.0 g (67.2 mmole) 5-benzyloxyindole in 75 ml sieve dried dimethylsulfoxide (DMSO) under nitrogen at room temperature was added in one portion 2.02 g (84 mmole, 1.25 equivalents) of 99% NaH. After stirring for 4.5 hours at room temperature, a solution of 10.17 g (84 mmole, 1.25 equivalents) 3-fluorobenzonitrile in 20 ml sieve dried DMSO was added dropwise over six minutes. The reaction mixture was permitted to stir overnight at room temperature and then was heated at 80°–90° C. for 2 hours. The cooled product was poured onto ice (100 ml) and extracted with chloroform. In order to clear an emulsion that formed at this point, a filtration through a pad of celite was necessary. The organic portion was washed successively with water, 2 N HCl, brine, dried over Na$_2$SO$_4$ and concentrated to give 22.01 g of product. Crystallization from hot glacial acetic acid afforded 19.46 g of a low melting (36°–40° C.) solvated product (nitrile:solvent=1:1–2.0). A 4.8 g portion of the recrystallized material was chromatographed on silica gel (ether-hexane) to give 3.0 g of 3-(5-benzyloxy-1-indolyl)benzonitrile.

ANALYSIS: Calculated for C$_{22}$H$_{16}$N$_2$O: 81.46%C, 4.97%H, 8.64%N, Found: 81.18%C, 5.03%H, 8.50%N.

b. 3-(5-Benzyloxy-1-indolinyl)benzonitrile

A cooled (17°–19° C.), rapidly stirred slurry of 16.2 g (49.9 mmole) of 3-(5-benzyloxy-1-indolyl)benzonitrile of Example 18a in 200 ml glacial acetic acid under nitrogen was treated portionwise with 9.73 g (3.1 equivalents, 154.8 mmole) sodium cyanoborohydride. After warming to room temperature and stirring overnight (about 16 hours) under nitrogen, the reaction mixture was poured onto 200 ml ice, carefully made basic using 50% NaOH, and extracted with methylene chloride. The organic portion was washed with water, brine, dried over Na$_2$SO$_4$, and concentrated to give 15.45 g (94.8%) of product. A 5.0 g portion was chromatographed on silica gel using ether-hexane to give 3.85 g (73% overall) of 3-(5-benzyloxy-1-indolinyl)benzonitrile, m.p. 101.5°–103.5° C. An analytical sample was prepared by recrystallization from ethyl acetate-hexane, m.p. 101° C.

ANALYSIS: Calculated for C$_{22}$H$_{18}$N$_2$O: 80.96%C, 5.56%H, 8.58%n, Found: 80.80%C, 5.59%H, 8.54%N.

c. N-Acetyl-3-(5-benzyloxy-1-indolinyl)benzenemethanamine

A solution of 1.52 g (4.7 mmole) of 3-(5-benzyloxy-1-indolinyl)benzonitrile of Example 18b in 60 ml acetic anhydride over 0.2 g Raney Nickel (#28 finely divided) and 0.76 g (9.3 mmole, 2 equivalents) sodium acetate was shaken at 50° C. under 50 psi of hydrogen until gas uptake had ceased and TLC analysis showed the reduction to be complete. The catalyst was filtered on a pad of celite and the filtrate was partitioned between chloroform (40 ml) and water (400 ml) and the combined organic portions were washed twice with water (600 ml), aqueous $NaHCO_3$ (two 600 ml portions) and brine, dried over $Na_2SO_4$, and concentrated to give an oil. Chromatography on silica gel (80 g) using 1–5% methanol in ether afforded 1.31 g (86.8%) of N-Acetyl-3-(5-benzyloxy-1-indolinyl)benzenemethanamine as an oil.

ANALYSIS: Calculated for $C_{24}H_{24}N_2O_2$: 77.39%C, 6.50%H, 7.52%N, Found: 77.15%C, 6.54%H, 7.39%N.

EXAMPLE 19

3-(5-Benzyloxy-1-indolinyl)benzenemethanamine hydrochloride

A solution of 2.82 g (8.64 mmole) of 3-(5-benzyloxy-1-indolinyl)benzonitrile of Example 18b in 20–25 ml distilled THF was added dropwise over twelve minutes to a rapidly stirred ice cold slurry of 1.31 g (34.56 mmole, 4.0 equivalents) $LiAlH_4$ in 35 ml distilled THF under nitrogen. After warming to room temperature, the mixture was heated under reflux for 2 hours, permitted to cool to room temperature, placed in an ice bath, and treated dropwise with 1.3 ml water, 1.3 ml 10% NaOH and 3.9 ml water. The salts were filtered and washed with 200 ml boiling methylene chloride. The filtrate was concentrated and the residue was dissolved in 100 ml $CH_2Cl_2$, washed with brine, dried over $Na_2SO_4$ and concentrated to give 2.37 g (83%) of crude free base. Conversion to the hydrochloride salt (dry ether-isopropanol/ethereal HCl) as in Example 1 and recrystallization from isopropanol containing 10–20% methanol gave 1.89 g (59.6%) of 3-(5-benzyloxy-1-indolinyl)-benzenemethanamine hydrochloride, m.p. 177°–180° C.

ANALYSIS: Calculated for $C_{22}H_{22}N_2O.HCl$: 72.02%C, 6.32%H, 7.64%N, Found: 72.18%C, 6.24%H, 7.57%N.

EXAMPLE 20 a. 3-(1-Indolinyl)benzoic acid

A mixture of 47.7 g (5.3 equivalents) KOH pellets and 30.0 g (0.136 mole) 3-(1-indolinyl)benzonitrile of Example 3a in 270 ml ethylene glycol was heated at 180° for 6 hours (the mixture became homogeneous at 150°C.). After cooling to room temperature, the product was poured onto a mixture of 400 ml ice/85 ml (ca. 1 mole) concentrated HCl and extracted with $CHCl_3$ (850 ml total). The organic portion was washed with water (750 ml), brine (600 ml), dried over $Na_2SO_4$, and concentrated to give 35.0 g of crude acid (theory=32.6 g).

Recrystallization from chloroform-toluene gave 19.43 g (59.7%), m.p. 166°–168.5° C. A second recrystallization of a 5.1 g portion gave 4.28 g of 3-(1-indolinyl)benzoic acid, m.p. 168°–170.5° C.

ANALYSIS: Calculated for $C_{15}H_{13}NO_2$: 75.30%C, 5.48%H, 5.85%N, Found: 75.12%C, 5.52%H, 5.83%N.

b. 3-(1-Indolinyl)benzenemethanol

A solution of 16.10 g (67.3 mmole) 3-(1-indolinyl)benzoic acid of Example 20a in 75 ml dry THF was added dropwise over seven minutes to a rapidly stirred, ice cold slurry of 2.55 g (67.3 mmole) lithium aluminum hydride in 50 ml dry THF. The ice bath was removed at the end of the addition and, after warming to room temperature, the reaction mixture was heated at reflux for 1 hour. The product was cooled to 0°–5° C. and treated dropwise with 3 ml water, 3 ml 10% aqueous NaOH and 9 ml water. The salts were filtered, washed 3 times with boiling chloroform (100 ml total), and the filtrate was concentrated. The residue was dissolved in chloroform, washed with brine, dried over $Na_2SO_4$, concentrated, and dried under high vacuum to give 14.42 g (95.1%) of an oil. Kugelrohr distillation of a 6.50 g portion afforded 5.75 g (83% overall yield) of 3-(1-indolinyl) benzenemethanol, b.p. 204°–208° C./0.13 mm.

ANALYSIS: Calculated for $C_{15}H_{15}NO$: 79.97%C, 6.71%H, 6.22%N, Found: 79.88%C, 6.43%H, 6.01%N.

c. 3-(1-Indolinyl)benzenemethanesulfonic acid methyl ester

A stirred solution of 8.11 g (36 mmole) of 3-(1-indolinyl)benzenemethanol of Example 20b and 7.6 ml (54 mmole) of triethylamine in 35 ml of methylene chloride ($CH_2Cl_2$) was cooled to 0° C. and then treated dropwise with a solution of 3.1 ml (40% mmole) of methanesulfonyl chloride in 35 ml of $CH_2Cl_2$. Ten minutes after the addition, 150 ml of water was added. The organic layer was separated, washed twice with 150 ml of cold 2N-HCl, then with 150 ml of saturated $NaHCO_3$, with 150 ml of brine, dried over $Na_2SO_4$ and concentrated in vacuo. This left 10.3 g (93.9% yield) of 3-(1-indolinyl)benzenemethanesulfonic acid methyl ester as an oil.

d. 3-(1-indolinyl)benzeneacetonitrile

A mixture of 10.2 g (ca. 33.8 mmole) of 3-(1-indolinyl) benzenemethanesulfonic acid methyl ester of Example 20c and 4.97 g (101.4 mmole, 3.0 equiv.) sodium cyanide in 200 ml sieve dried DMF was heated at 60°–70° C. for 50 minutes. The product was concentrated under high vacuum at 50°–60° C. and the residue was partitioned between chloroform (200 ml) and water (200 ml). The organic portion was washed twice with 200 ml water, 200 ml brine, dried over $Na_2SO_4$ and concentrated under vacuum to give 6.39 g (80.7%) of product. Kugelrohr distillation of a 0.8 g sample gave 0.6 g of an oil 3-(1-indolinyl)benzeneacetonitrile, b.p. 189°–192° C./0.15 mm.

ANALYSIS: Calculated for $C_{16}H_{14}N_2$: 82.02%C, 6.02%H, 11.96%N, Found: 81.85%C, 5.93%H, 12.14%N.

e. N-Acetyl-2-[3-(1-indolinyl)]benzeneethanamine

A sample of 0.37 g (wet wt.) #28 finely divided Raney Nickel catalyst was carefully washed thrice with absolute ethanol and thrice with acetic anhydride. The moist catalyst was then added to a solution of 2.0 g (8.54 mmoles) of 3-(1-indolinyl)benzeneacetonitrile of Example 20d in 50 ml acetic anhydride over 1.05 g (1.5 equivalents, 12.81 mmole) sodium acetate (anhydrous powder) in a 500 ml Parr bottle. The mixture was shaken at 50° C. under 50 psi $H_2$ until gas uptake ceased and TLC analysis showed no starting material was present. The catalyst was filtered on a pad of celite and the filtrate was concentrated to give 2.37 g (100%) of the product as an oil. Chromatography on 45 g of silica gel using increasingly polar mixtures of ether-hexane then methanol-ether afforded 1.62 g (67.8% overall) of N-acetyl-2-[3-(1-indolinyl)]benzeneethanamine as an oil.

ANALYSIS: Calculated for $C_{18}H_{20}N_2O$: 77.11%C, 7.19%H, 9.99%N, Found: 77.38%C, 7.04%H, 9.96%N.

f. 3-(1-Indolinyl)-2-benzeneethanamine.1/2 fumarate

A mixture of 5.97 g (21.29 mmole) of N-acetyl-2-[3-(1-indolinyl)]benzeneethanamine of Example 20e, 4.78 g (4 equivalents, 85.17 mmole) 85% KOH pellets, 5 ml water, and 85 ml ethylene glycol was heated at 160°–180° C. for 4 hours. The product was poured onto ice and extracted three times with chloroform (200 ml total). The combined organic extracts were washed with water (250 ml), brine (250 ml), dried ($Na_2SO_4$) and concentrated to give 4.89 g (96.4%) of the crude free base as an oil. A warm solution of fumaric acid (2.38 g, 20.5 mmole) in absolute ethanol (35 ml) was treated with a filtered solution of the free base (4.89 g, 20.5 mmole) in absolute ethanol (30 ml). The pure fumarate salt crystallized slowly upon standing overnight in the cold. The crystals were collected, washed with absolute ethanol, then with dry ether and dried to give 4.51 g (74.2%) of 3-(1-indolinyl)-2-benzeneethanamine.1/2 fumarate, m.p. 191°–193° C.

ANALYSIS: Calculated for $C_{16}H_{18}N_2.1/2C_4H_4O_4$: 72.95%C, 6.80%H, 9.45%N, Found: 73.09%C, 6.40%H, 9.25%N.

EXAMPLE 21

3-(1-Indolinyl)-α-methylbenzenemethanamine hydrochloride

A solution of 5.07 g (23.02 mmole) of 3-(1-indolinyl)-benzonitrile of Example 3a in 50 ml distilled THF was added dropwise over 36 minutes to an ice cold stirred solution of 2.74 M (16.8 ml, 2.0 equivalents, 45 mmole) methyl magnesium chloride in tetrahydrofuran (THF) under nitrogen. At the end of the addition the product was permitted to warm to room temperature. After heating at 60° C. for 2 hours, the mixture was cooled in an ice bath and treated with an ice cold slurry of 1.75 g (46 mmole) $LiAlH_4$ in 75 ml distilled THF. Upon warming to room temperature, the reaction mixture was heated under reflux for 1 hour, cooled in an ice bath, treated dropwise with 2 ml ice water, 2 ml 10% NaOH, and 6 ml water. The salts were filtered, washed four times with boiling methylene chloride (350 ml total) and the filtrate was concentrated. The residue was dissolved in chloroform, washed with brine, dried over $Na_2SO_4$ and concentrated to give 4.83 g (88.0%) of free base as an oil. Conversion of a 6.7 g sample of free base (from two separate preparations) to the hydrochloride salt (ether/ethanol HCl) as in Example 1 and recrystallization from ethanol-ethyl acetate afforded 3.18 g (36%) of 3-(1-indolinyl)-α-methylbenzenemethanamine hydrochloride, m.p. 223.0°–225.5° C.

ANALYSIS: Calculated for $C_{16}H_{18}N_2.HCl$: 69.93%C, 6.97%H, 10.19%N, Found: 69.77%C, 6.99%H, 10.02%N.

EXAMPLE 22

3-(1-Indolinyl)-α-phenylbenzenemethanamine hydrochloride

A solution of 3.0 g (13.6 mmole) of 3-(1-indolinyl) benzonitrile of Example 3a in 15 ml THF was added dropwise over 17 minutes to an ice cooled, magnetically stirred solution of 2.8 M (10–11 ml, ca. 2 equivalents, 27.2 mmole) phenyl magnesium bromide in ether. The mixture was permitted to warm to room temperature, and then heated at 50°–60° C. for 1.75 hours. After cooling to 0°–5° C., the stirred product was treated with an ice cold slurry of 1.03 g (27.2 mmole) $LiAlH_4$ in 15 ml THF. The resulting slurry was heated at 60° C. for 2.5 hours, cooled to 0°–5° C., and treated dropwise with 1 ml water, 1 ml 10% NaOH and 5 ml water. The salts were filtered, washed with boiling methylene chloride and the filtrate was concentrated. The residue was dissolved in chloroform, washed with brine, dried over $Na_2SO_4$, and concentrated to give 3.89 g (95.1%) of the crude free base as an oil. Conversion to the hydrochloride salt (ether/ethereal HCl) as in Example 1, and recrystallization from ethanol-ethyl acetate afforded 2.43 g (53.0%) of 3-(1-indolinyl)-α-phenylbenzenemethanamine hydrochloride, m.p. 244.0°–245.5° C.

ANALYSIS: Calculated for $C_{21}H_{20}N_2.HCl$: 74.88%C, 6.28%H, 8.32%N, Found: 74.61%C, 6.36%H, 8.34%N.

EXAMPLE 23

α-(5-Methoxy-1-indolinyl)-m-tolunitrile

An ice cold slurry of 5.89 g (42.6 mmole) of $K_2CO_3$ and 5.3 g (35.5 mmole) of 5-methoxyindoline in 55 ml of DMF was treated dropwise with a solution of 7.28 g (37.3 mmole) of α-bromo-m-tolunitrile in 50 ml of DMF. After stirring for 1 hour at room temperature, the reaction mixture was concentrated under high vacuum. The residue was partitioned between methylene chloride (250 ml) and water (250 ml). The organic layer was separated, washed with 5% NaOH (300 ml), brine (300 ml), dried over $Na_2SO_4$ and concentrated under vacuum to yield 9.28 g (98.9% yield) of α-(5-methoxy-1-indolinyl)-m-tolunitrile.

b.

3-(5-Methoxy-1-indolinylmethyl)benzenemethanamine dihydrochloride

A solution of 4.85 g (18.35 mmole of α-(5-methoxy-1-indolinyl)-m-tolunitrile of Example 23a in 45 ml THF was added dropwise over 40 minutes to an ice cold, rapidly stirred slurry of 2.79 g (73.4 mmole, 4 equivalents) $LiAlH_4$ in THF under nitrogen. After heating under reflux for 1 hour the reaction mixture was cooled to 0°–5° C. and treated dropwise with 3 ml ice water, 3 ml 10% NaOH and 8 ml water. The salts were filtered, washed twice with warm chloroform (250 ml total), and the filtrate was concentrated. The residue was dissolved in chloroform, washed with brine, dried over $Na_2SO_4$, and concentrated to give 4.47 g (90.8%) of crude free base. Conversion to the hydrochloride salt (ether/ethereal HCl) as in Example 1 afforded 4.84 g (77.3%). Recrystallization from n-butanol gave 3.62 g (57.9% overall) of 3-(5-methoxy-1-indolinylmethyl)benzenemethanamine dihydrochloride, m.p. 167° C., dec.

ANALYSIS: Calculated for $C_{17}H_{20}N_2O.2HCl$: 59.83%C, 6.50%H, 8.21%N, Found: 59.84%C, 6.78%H, 8.04%N.

We claim:

1. A compound having the formula

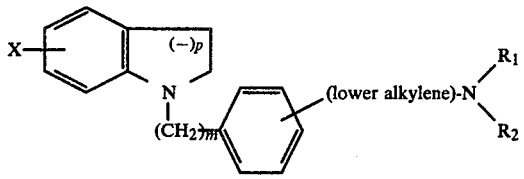

where R₁ and R₂ are the same or different and are hydrogen, lower alkyl, cycloalkyl and acyl of the formula

where R₃ is lower alkyl, lower alkoxy, cycloalkyl, phenyl of the formula

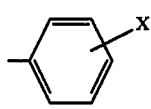

and Ar lower alkyl of the formula

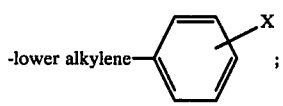

X is hydrogen, halogen, lower alkoxy, Ar lower alkoxy of the formula

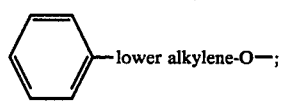

m and p are independently an integer of 0 or 1 and the pharmaceutically acceptable acid addition salts thereof.

2. The compound as defined in claim 1 wherein p is 0.

3. The compound as defined in claim 1 which is 2-(1-indolinyl)benzenemethanamine or a pharmaceutically acceptable salt thereof.

4. The compound as defined in claim 1 which is 4-(1-indolinyl)benzenemethanamine or a pharmaceutically acceptable salt thereof.

5. The compound as defined in claim 1 which is 3-(1-indolinyl)benzenemethananmine or a pharmaceutically acceptable salt thereof.

6. The compound as defined in claim 1 which is 3-(5-chloro-1-indolinyl)benzenemethanamine or a pharmaceutically acceptable salt thereof.

7. The compound as defined in claim 1 which is 3-(1-indolinyl)-N-methylbenzenemethanamine or a pharmaceutically acceptable salt thereof.

8. The compound as defined in claim 1 which is 3-(5-methoxy-1-indolinyl)benzenemethanamine or a pharmaceutically acceptable salt thereof.

9. The compound as defined in claim 1 which is N-cyclopropyl carbonyl-3-(1-indolinyl)benzenemethanamine.

10. The compound as defined in claim 1 which is 3-(1-indolinyl)-N-phenylacetylbenzenemethanamine.

11. The compound as defined in claim 1 which is N-cyclopropylmethyl-3-(1-indolinyl)benzenemethanamine or a pharmaceutically acceptable salt thereof.

12. The compound as defined in claim 1 which is 3-(1-indolinyl)-N-(2-phenylethyl)benzenemethanamine or a pharmaceutically acceptable salt thereof.

13. The compound as defined in claim 1 which is N-ethoxycarbonyl-3-(1-indolinyl)-N-methylbenzenemethanamine.

14. The compound as defined in claim 1 which is N,N-dimethyl-3-(1-indolinyl)benzenemethanamine or a pharmaceutically acceptable salt thereof.

15. The compound as defined in claim 1 which is 3-(5-benzyloxy-1-indolinyl)benzenemethanamine or a pharmaceutically acceptable salt thereof.

16. The compound as defined in claim 1 which is N-acetyl-2-[3-(1-indolinyl)benzeneethanamine.

17. The compound as defined in claim 1 which is 3-(1-indolinyl)-α-methylbenzenemethanamine or a pharmaceutically acceptable salt thereof.

18. The compound as defined in claim 1 which is 3-(1-indolinyl)-2-benzeneethanamine or a pharmaceutically acceptable salt thereof.

19. The compound as defined in claim 1 which is 3-(indolinyl)-α-phenylbenzenemethanamine or a pharmaceutically acceptable salt thereof.

20. The compound as defined in claim 1 which is N-ethoxycarbonyl-3-(1-indolinyl)benzenemethanamine.

21. The compound as defined in claim 1 wherein m is 1.

22. The compound as defined in claim 21 which is 3-(1-indolinylmethyl)benzenemethanamine or a pharmaceutically acceptable acid addition salt thereof.

23. The compound as defined in claim 21 which is 3-(5-chloro-1-indolinylmethyl)benzenemethanamine or a pharmaceutically acceptable acid addition salt thereof.

24. The compound as defined in claim 21 which is 3-(5-methoxy-1-indolinylmethyl)benzenemethanamine or a pharmaceutically acceptable acid addition salt thereof.

25. The compound as defined in claim 1 wherein p is 1.

26. The compound as defined in claim 25 which is 3-(5-chloro-1-indolyl)benzenemethanamine or a pharmaceutically acceptable acid addition salt thereof.

27. The compound as defined in claim 25 which is 3-(1-indolyl)benzenemethanamine or a pharmaceutically acceptable acid addition salt thereof.

28. The compound as defined in claim 25 which is 3-(5-methoxy-1-indolyl)benzenemethanamine or a pharmaceutically acceptable acid addition salt thereof.

29. The compound as defined in claim 25 which is N-acetyl-3-(5-benzyloxy-1-indolinyl)benzenemethanamine.

30. An analgesic composition comprising an effective pain relieving amount of a compound having the formula

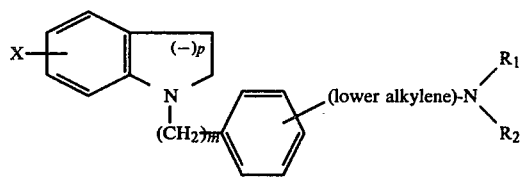

where $R_1$ and $R_2$ are the same or different and are hydrogen, lower alkyl, cycloalkyl and acyl of the formula

where $R_3$ is lower alkyl, lower alkoxy, cycloalkyl, phenyl of the formula

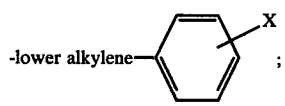

and Ar lower alkyl of the formula

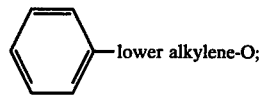

X is hydrogen, halogen, lower alkoxy, and Ar lower alkoxy of the formula

m and p are independently an integer of 0 or 1 and the pharmaceutically acceptable acid addition salts thereof.

31. A method of alleviating pain in a mammal which comprises administering to a mammal a pain alleviating amount of a compound of the formula

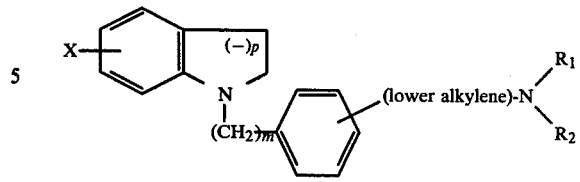

where $R_1$ and $R_2$ are the same or different and are hydrogen, lower alkyl, cycloalkyl and acyl of the formula

where $R_3$ is lower alkyl, lower alkoxy, cycloalkyl, phenyl of the formula

and Ar lower alkyl of the formula

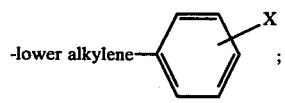

X is hydrogen, halogen, lower alkoxy and Ar lower alkoxy of the formula

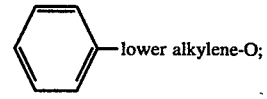

m and p are independently an integer of 0 or 1 and the pharmaceutically acceptable acid addition salts thereof.

* * * * *

UNITED STATES PATENT AND TRADEMARK OFFICE
CERTIFICATE OF CORRECTION

PATENT NO. : 4,448,784

DATED : May 15, 1984

INVENTOR(S) : Edward J. Glamkowski et al.

It is certified that error appears in the above—identified patent and that said Letters Patent is hereby corrected as shown below:

Abstract: 2nd Column - 2nd structure from bottom:
"-lower alkylene" should be deleted from sentence above;

Column 7, line 57:  "2-(1-Indolinyl..." should be
 --a.  2-(1-Indolinyl...--;

Column 8, line 7:  "2-(1-Indolinyl..." should be
 --b.  2-(1-Indolinyl...--;

Column 8, line 37:  "4-(1-Indolinyl..." should be
 --a.  4-(1-Indolinyl...--;

Column 9, Example 3: line 19 - "3-(1-Indolinyl..." should be
 --a.  3-(1-Indolinyl...--;

Column 9, Example 3: line 38 - "3-(1-Indolinyl..." should be
 --b.  3-(1-Indolinyl...--;

Column 9, Example 4: line 63 - "3-(5-Chloro..." should be
 --a.  3-(5-Chloro...--;

UNITED STATES PATENT AND TRADEMARK OFFICE
CERTIFICATE OF CORRECTION

PATENT NO. : 4,448,784

DATED : May 15, 1984

INVENTOR(S) : Edward J. Glamkowski et al.

It is certified that error appears in the above—identified patent and that said Letters Patent is hereby corrected as shown below:

Column 15, Example 11, line 25: "ml (76,34 mmole..." should be --ml (76.34 mmole...--;

Column 20, Example 20c, line 30: "(40% mmole)" should be --(40 mmole)--;

Column 22, Example 23, line 27: "a." is missing and should be inserted.

Signed and Sealed this

Twelfth Day of February 1985

[SEAL]

Attest:

DONALD J. QUIGG

Attesting Officer     Acting Commissioner of Patents and Trademarks